(12) United States Patent
Tornier et al.

(10) Patent No.: US 6,328,758 B1
(45) Date of Patent: Dec. 11, 2001

(54) SUTURE ANCHOR WITH REVERSIBLE EXPANSION

(75) Inventors: Alain Tornier, Saint Ismier; Francois Bonnomet, Strasbourg, both of (FR)

(73) Assignee: Tornier SA, Saint Ismier (FR)

( * ) Notice: Subject to any disclaimer, the term of this patent is extended or adjusted under 35 U.S.C. 154(b) by 0 days.

(21) Appl. No.: 09/673,754

(22) PCT Filed: Apr. 21, 1999

(86) PCT No.: PCT/FR99/00941

§ 371 Date: Nov. 27, 2000

§ 102(e) Date: Nov. 27, 2000

(87) PCT Pub. No.: WO99/53844

PCT Pub. Date: Oct. 28, 1999

(30) Foreign Application Priority Data

Apr. 21, 1998 (FR) .................................................. 98 05203

(51) Int. Cl.⁷ .................................................. A61B 17/04
(52) U.S. Cl. .......................................................... 606/232
(58) Field of Search ............................... 606/232, 72, 74, 606/75

(56) References Cited

U.S. PATENT DOCUMENTS

| 5,248,231 | * | 9/1993 | Denham et al. ........................ 411/43 |
| 5,268,001 | * | 12/1993 | Nicholson et al. ..................... 606/72 |
| 5,326,205 | * | 7/1994 | Anspach, Jr. et al. ................... 606/74 |
| 5,464,427 | * | 11/1995 | Curtis et al. . |
| 5,472,452 | | 12/1995 | Trott ....................................... 606/232 |
| 5,480,403 | * | 1/1996 | Lee et al. . |
| 5,486,197 | * | 1/1996 | Lee et al. ................................ 606/72 |
| 5,501,695 | | 3/1996 | Anspach, Jr. et al. ............... 606/232 |
| 5,522,845 | * | 6/1996 | Wenstrom, Jr. ....................... 606/232 |
| 5,545,180 | * | 8/1996 | Lee et al. .............................. 606/232 |
| 5,571,104 | * | 11/1996 | Li ........................................... 606/232 |
| 5,649,963 | | 7/1997 | McDevitt ............................. 606/232 |

FOREIGN PATENT DOCUMENTS 2173565A  10/1986  (GB) .

* cited by examiner

Primary Examiner—Gary Jackson
(74) Attorney, Agent, or Firm—Dowell & Dowell, P.C.

(57) ABSTRACT

A suture anchor for fixing soft tissues against a bone, including a hollow body having expanding elements limited in their plastic deformation, when an external traction force (T) is applied for fixing the suture anchor in the bone by stop means and wherein the expanding elements are reversibly deformed when another external thrust force (P) is applied thereto so that the suture anchor may be removed from the bone.

15 Claims, 15 Drawing Sheets

SUTURE ANCHOR WITH REVERSIBLE EXPANSION

BACKGROUND OF THE INVENTION

1. Field of the Invention

This invention relates to a suture anchor that allows to connect soft tissues, such as ligaments or tendons, to the bone and, in particular, to mend rotator cuffs and Bankart's lesions.

2. Description of Related Art

In U.S. Pat. No. 5,501,695, in the name of Anspach, is disclosed a two part suture anchor that allows a muscular and tendinous reinsertion into the bone.

This suture anchor includes a first external, cylindrical element attached to the fixation prongs that are separated from each other by means of grooves that are parallel to the longitudinal axis of the suture anchor. The first element houses in its interior a second deformation element that acts in conjuncture with the free element of the fixation prongs The second deformation element is attached by means of a fracture zone of a dragbar that enables the surgeon, after having introduced the suture anchor into a hole previously drilled into the bone, to slide this second element into the first one in order to axially deform the fixation prongs in the spongy part of the bone.

Since the tension force suffices to deform the fixation prongs, the rod separates from the second element through an irreversible break.

It can be noted that the prongs deform laterally following a direction approximately perpendicular to the longitudinal axis of the suture anchor in order to permanently attach the latter to the inside of the bone.

Lastly, the first element is attached at one of its extremities to a flange that comes to rest against the cortical bone and is provided with a series of holes, used by the surgeon for the attaching of the suture threads.

The above-described suture anchor presents some disadvantages, namely that it is not designed to be removed without causing a complete destruction of the bone or bones to which it is attached. In fact, the anchor is not provided with any means of removal that would allow it to be dislodged from the bone without causing any damage to the bone.

Moreover, beyond the fracture zone of the second element, the suture anchor is not provided with means limiting the displacement of the element in order to prevent the fixation prongs from abnormally breaking under the effects of the tractive force.

Also, U.S. Pat. No. 5,649,963 discloses a suture anchor and an element onto which is screwed a bushing for the attaching of the anchor.

The suture anchor is provided with expansion means that move towards the outside under the pressure of the bushing and the element. It can be noted that the element is provided with a device that allows that the expansion means come together so that they can be removed from the suture anchor.

It can be seen that the suture anchor Is not provided with stop means limiting the deformation of the expansion means when the pressure of the bushing and the element is applied.

U.S. Pat. No. 5,472,452 discloses a suture anchor provided with elastic deformation expansion means and a deformation element guided inside of a hollow body of the anchor to deform the expansion means.

The deformation element presents a specific shape that, being under tractive force, causes the deformation of the elastic expansion means so that they penetrate into the spongy bone, that is near the hole into which was previously introduced the suture anchor.

The deformation element has a specific shape that causes the expansion means be blocked in a position that holds the suture anchor in the spongy bone.

Under the effect of a thrust force, the deformation element penetrates into the suture anchor body to deform anew the expansion means in a direction identical to that of the tractive force.

It can be observed that when the suture anchor is removed, the expansion means penetrate deeper into the spongy bone, entailing the risk that the return of the expansion means to their original position is prevented, which position is obtained due to the elastic characteristics of the expansion means.

GB Patent 2 173 565 discloses a surgical screw constituted by several components that interact to allow the deformation of an expansion means made out of a high-density plastic material.

The surgical screw comprises a hollow, cylindrical body traversed by a threaded element provided with a head, an adjusting nut interacting with the threaded element, and expansion means provided between the cylindrical body and the head of the adjusting nut.

When the threaded element is being turned, the nut penetrates into the hollow body in order to deform the expansion means that are affixed to the head of the nut.

It can be noted that the screw described in patent GB 2 173 565 is not a monobloc, that is to say, that it does not consist of one only piece, and that the expansion means do not have plastic deformation characteristics due to the utilized material.

This invention has the aim to specifically remedy these disadvantages.

SUMMARY OF THE INVENTION

The suture anchor in accordance with the present invention has the object of being reversible in order to allow its extraction from the bone without having to drill a hole of a larger diameter than that of the deformed prongs.

The suture anchor in accordance with the present invention, allowing the attaching of soft tissues to a bone, comprises a single-piece hollow body that is provided with expansion means that are limited in their plastic deformation by stop means when an external tractive force is applied for the attaching of the suture anchor to the bone, so that the deformation of the expansion means is reversible when another external thrust force is applied for the removal of the suture anchor from the bone.

The suture anchor in accordance with the present invention also includes means of fixation for holding of soft tissues against the bone.

The suture anchor in accordance with the present invention comprises a hollow body that is provided at one of its extremities with a head which, in turn, is provided with means of fixation for soft tissues to the bone, with expansion means that are constituted by at last two fixation prongs fastened on an extension of the head and parallel to a longitudinal axis of the body prior to its deformation. At least two stops are inserted between each prong of fixation and limit the plastic deformation of the latter, while on the other extremity the anchor has a conically shaped point.

The suture anchor in accordance with the present invention further comprises a head which, in turn, is provided with means of fixation that are constituted by two tongues facing and parallel to the longitudinal axis of the hollow body, prior to deformation, in order to delimit an oblong clearance that is traversed by at least one suture thread, which suture thread is fastened at the head after the deformation of the tongues due to a tractive force for the binding of the soft tissues to the suture anchor.

The suture anchor in accordance with the present invention also has a head which, in turn, is provided with means of fixation that are constituted by a disk that is fastened perpendicular to the longitudinal axis of the hollow body, which disk is shaped in such a manner as to fasten the soft tissues to the bone.

The suture anchor in accordance with the present invention also has a hollow body that, at the conical point, is provided with a threaded blind hole for the taking up of a threaded rod of an attachment to deform, on the one hand, by means of a tractive force, the prongs of fixation in an essentially perpendicular direction to the longitudinal axis of the body and, on the other hand, to deform the means of fixation through a second tractive force greater than the first one.

The suture anchor in accordance with the present invention also has a hollow body that is provided in the proximity of the head with a threaded internal borehole intended to take up a first threaded hollow rod of an attachment while a second rod sliding inside the first rod comes to rest at the bottom of a threaded blind hole in order to open, under the effect of a thrust force, the prongs of fixation to a position essentially stretching along the original one, in order to be able to remove the suture anchor from the bone.

The suture anchor in accordance with the present invention also has fixation prongs that are connected to a cylindrical section of the head and at the conical point by first bending fasteners in direction of the center of the body.

The suture anchor in accordance with the present invention also includes fixation prongs that present, respectively, in their center a second bending fastener that is inverted with respect to the first bending fasteners, so that each prong is constituted by two identical segments.

The suture anchor in accordance with the present invention further has an internal threaded borehole and a threaded blind hole that are provided on the same longitudinal axis of the body and are of different diameters.

The suture anchor in accordance with the present invention also has stops that extend parallel to the longitudinal axis of the body and whose lengths depend on the deformation one wishes to obtain from the fixation prongs.

The suture anchor in accordance with the present invention also includes a conical point that presents a side that is perpendicular to the axis.

The suture anchor in accordance with the present invention also has means of fixation whose oblong clearance is positioned in such a manner that its direction of the greatest length is perpendicular to the longitudinal axis of the body.

The suture anchor in accordance with the present invention further includes a head that comprises a cylindrical section provided with on its external periphery with a round flange adapted to constitute a support plate of the body against the external wall of the bone.

The suture anchor in accordance with the present invention also includes a head that presents a cylindrical section provided with an internal borehole of which a threaded section is in the proximity of the disk.

BRIEF DESCRIPTION OF THE DRAWINGS

The below description, taking into account the accompanying drawings, given as not limiting examples, allows a better understanding of the invention, of its characteristics and of the advantages it may provide.

DETAILED DESCRIPTION OF THE INVENTION

Figure 1:
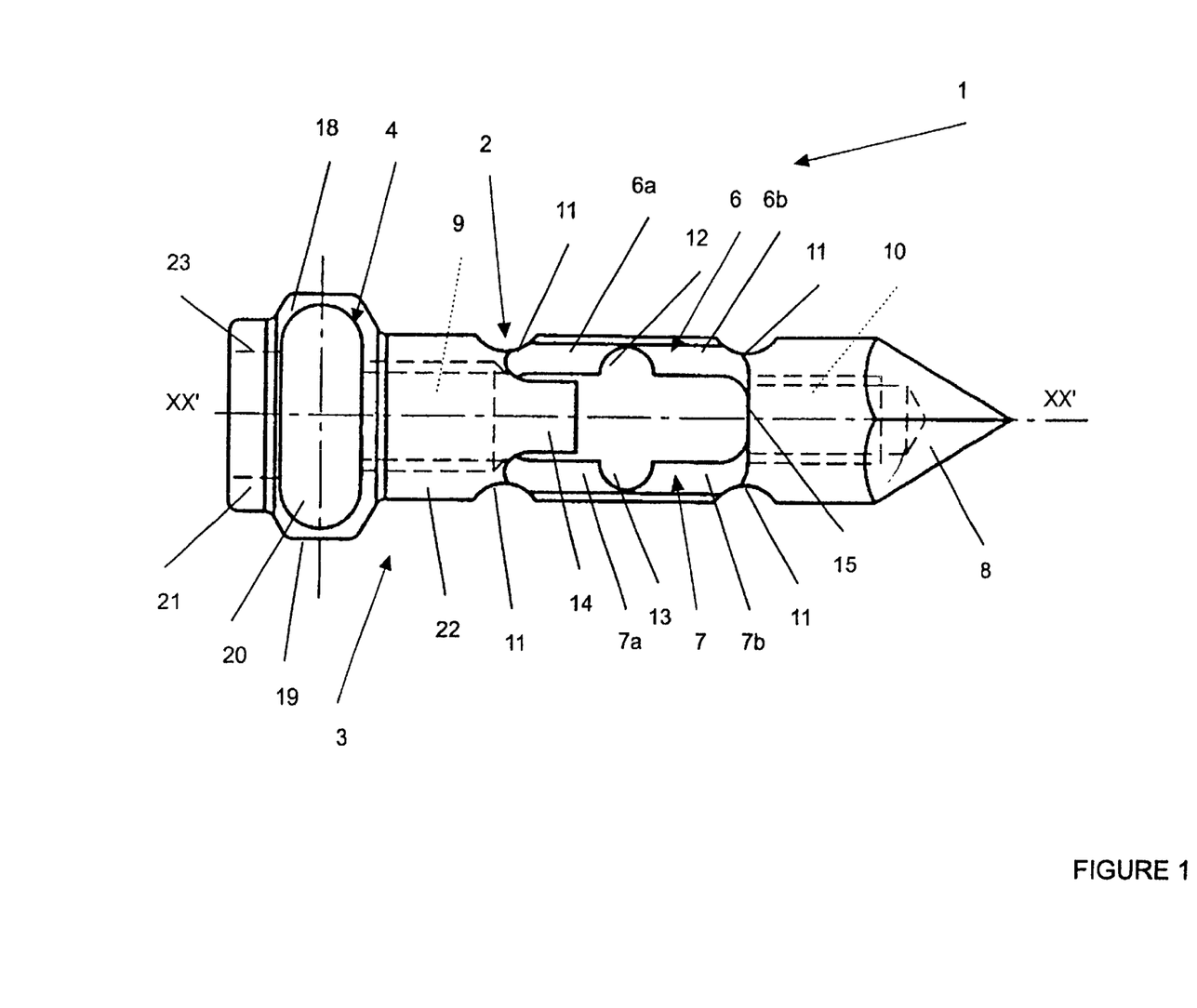
FIG. 1 is a view illustrating the suture anchor in accordance with the present invention.
Figure 2:
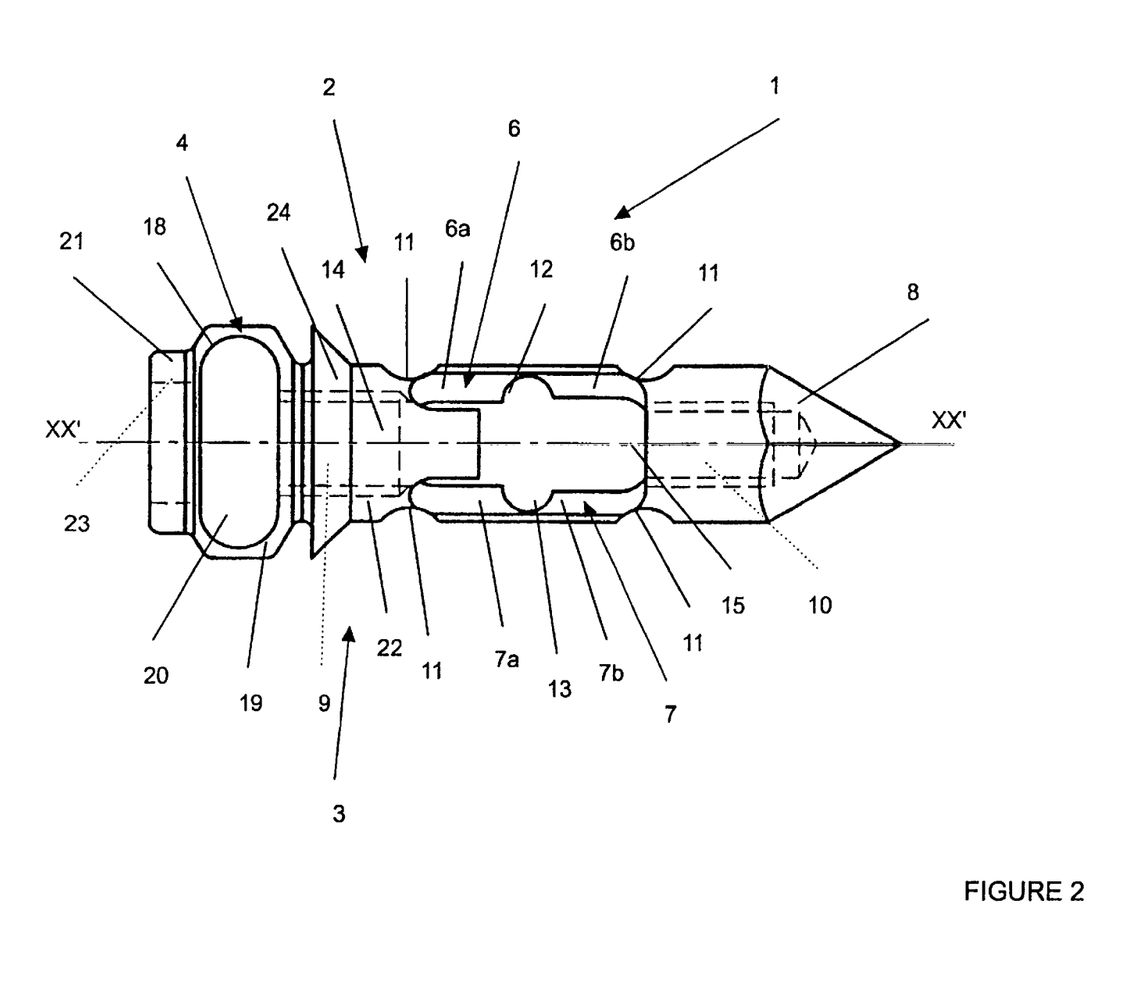
FIG. 2 is a view similar to that of FIG. 1 but illustrating a variant of the suture anchor in accordance with the present invention.

FIGS. 1 and 2 illustrate a monobloc suture anchor 1 comprising an elongated, hollow cylindrical body 2 susceptible to be plastically deformed, that can be put in place by means of arthroscopy in the surgical location.

The body 2 is provided at one of its extremities with a head 3 which, in turn, is provided with means of fixation 4 for the soft tissues 16 to the bone 17 of a patient by means of one or several suture threads 5 fastened on the head.

The head 3 is constituted by means of fixation 4 that are provided between a cylindrical support surface 21 and a cylindrical section 22.

The cylindrical section 22 of head 3 extends on the opposite side of the means of fixation 4 by means of at least two fixation prongs 6, 7 that, prior to deformation, run parallel to the longitudinal axis XX' of the body 2.

The other extremity of the body 2, opposite to that of the head 3, is constituted in the extension of the prongs 6 and 7 by a conically shaped point 8 that facilitates the setting in place of the suture anchor in the bone 17.

The cylindrical section 22 of the head 3 is provided with an internal threaded borehole 9 that opens, on the one hand, on the side of the means of fixation 4 and, on the other hand, between the fixation prongs 6 and 7. The threaded borehole 9 is provided along the longitudinal axis XX' of the body 2.

Th conical point 8 also has on its inside a threaded blind hole 10 that opens between the fixation prongs 6 and 7 and is provided on the same longitudinal axis XX' as that of the borehole 9. Besides, the diameter of the threaded borehole 9 is greater than that of the threaded hole 10.

The prongs 6 and 7 are connected to the head 3 and to the point 8 by means of bending fasteners 11 oriented towards the center of the body 2 allowing the deformation of the mentioned prongs under the effect of a tractive force.

The prongs 6 and 7 comprise in their center bending fasteners 12, 13, respectively, that are inverted with respect to the ones 11, so that each prong is constituted by two identical segments 6a, 6b and 7a, 7b.

Between each prong 6 and 7 are provided stop means 14 affixed to the cylindrical section 22 of the head 3 running in the direction of the conical point 8. Each stop 14 extends parallel to the longitudinal axis XX' of the body 2 and has a length that depends on the deformation one wishes to obtain from prongs 6 and 7.

In fact, the plastic deformation of the prongs 6 and 7 is limited by the stops 14 that come to rest against a surface 15 of the conical point 8. The surface 15 is on a plane perpendicular to the one of the axis XX' of the body 2.

The means of fixation 4 are constituted by two tongues 18, 19 opposite and parallel to the longitudinal axis XX' of the body 2, prior to their deformation. The tongues 18 and 19 delimit an oblong clearance 20 that enables the surgeon to pass at least one suture thread 5 at the surgical location.

The oblong clearance 20 of the means of fixation is positioned in such a manner that the direction of its greatest length is perpendicular to the longitudinal axis XX' of the body 2 of the suture anchor 1.

The supporting surface 21, bringing together the tongues 18, 19 opposite the cylindrical section 22, is provided with a borehole 23, coaxial to the threaded one 9, that opens, on the hand, to the exterior of the body 2 and, on the other hand, between the tongues, to be positioned opposite the mentioned threaded borehole 9 of the cylindrical section 22.

The cylindrical section 22 of the head 3 is provided on its external periphery and between the means of fixation 4 and the prongs 6,7 with a circular flange 24 forming a support stop for the body 2 against the external wall of the bone 17 when the suture anchor 1 is inserted into the latter (FIG. 2). The flange 24 is of conical shape that comes into contact with the bone 17 to serve as a stop at the time of placing the means of fixation 6 and 7.

Figure 3:
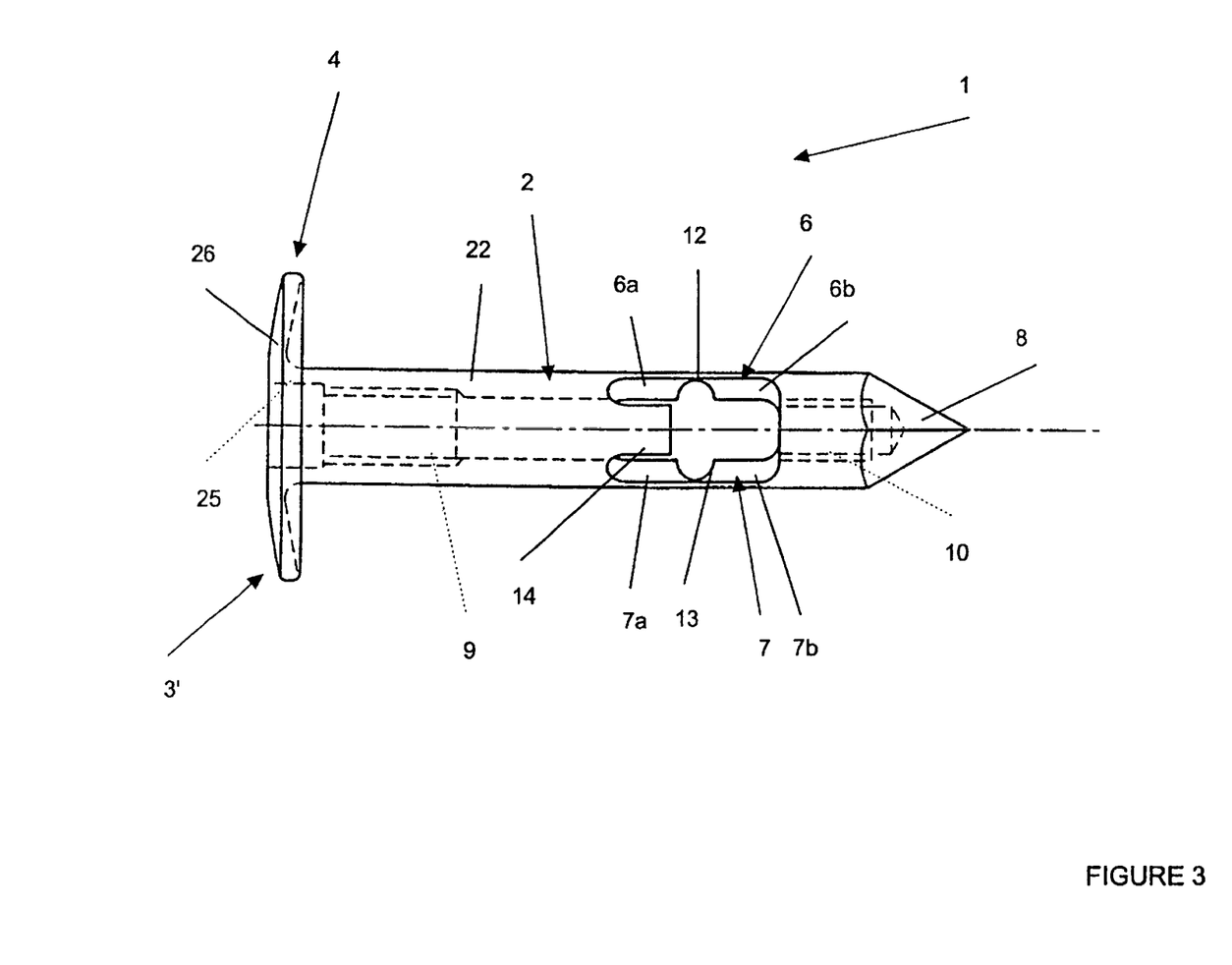
FIG. 3 is a view illustrating another variant of the suture anchor in accordance with the present invention.

In FIG. 3 is represented a variant of the suture anchor 1, of which the cylindrical body 2 has a head 3' that differs from the head 3, described above, with respect to the means of fixation 4 of the soft tissues.

The head 3' is constituted by a cylindrical section 22 longer than the one described above and into which Is drilled the internal and threaded borehole 9. This hole opens, on the one hand, between the prongs 6, 7 and, on the other hand, to the exterior of the body 2 at the means of fixation 4 by means of a coaxial borehole 25.

The internal borehole 9 is provided along its length with a threaded section that is shorter than the one shown in FIGS. 1 and 2. Furthermore, in this embodiment, it can be noted that the threaded portion of the internal borehole 9 is removed from the stops 14 because it is in the proximity of the means of fixation 4 due to the fact that the cylindrical section 22 is longer.

The means of fixation 4 are constituted at the extremity of the cylindrical section 22 of the head 3' and, opposite the prongs 6, 7, by a disk 26 that can be shaped so as to allow the retention of the soft tissues 16 against the bone 17.

In FIGS. 4a to 4d are illustrated the various stages for the setting into place the above-described suture anchor 1 into the bone 17 for the fixation of the soft tissues 16.

Figure 4A:
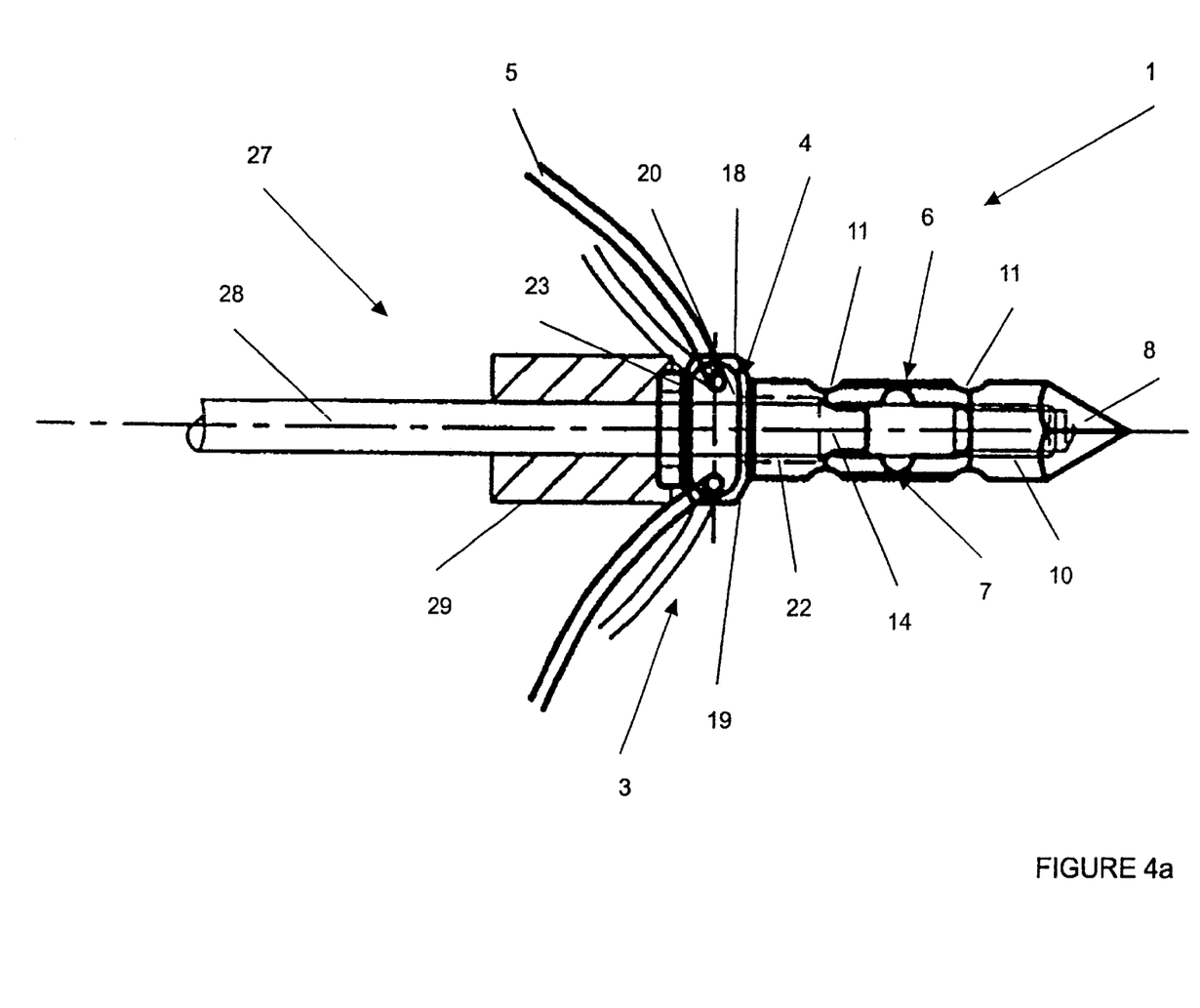
FIGS. 4a to 4d are diagrammatic views illustrating the embodiment of the suture anchor of FIGS. 1 and 2, being placed in a bone for the reinsertion of the soft tissues.

In FIG. 4a is illustrated the suture anchor 1 with its attachment 27 for the setting into place, that is constituted, by way of example, by a rod 28 that traverses the body 2 to screw into the blind hole 10 of the conical point 8. The rod 28 is affixed to a sleeve 29 that rests against the surface 23 of the head 3.

Figure 4B:
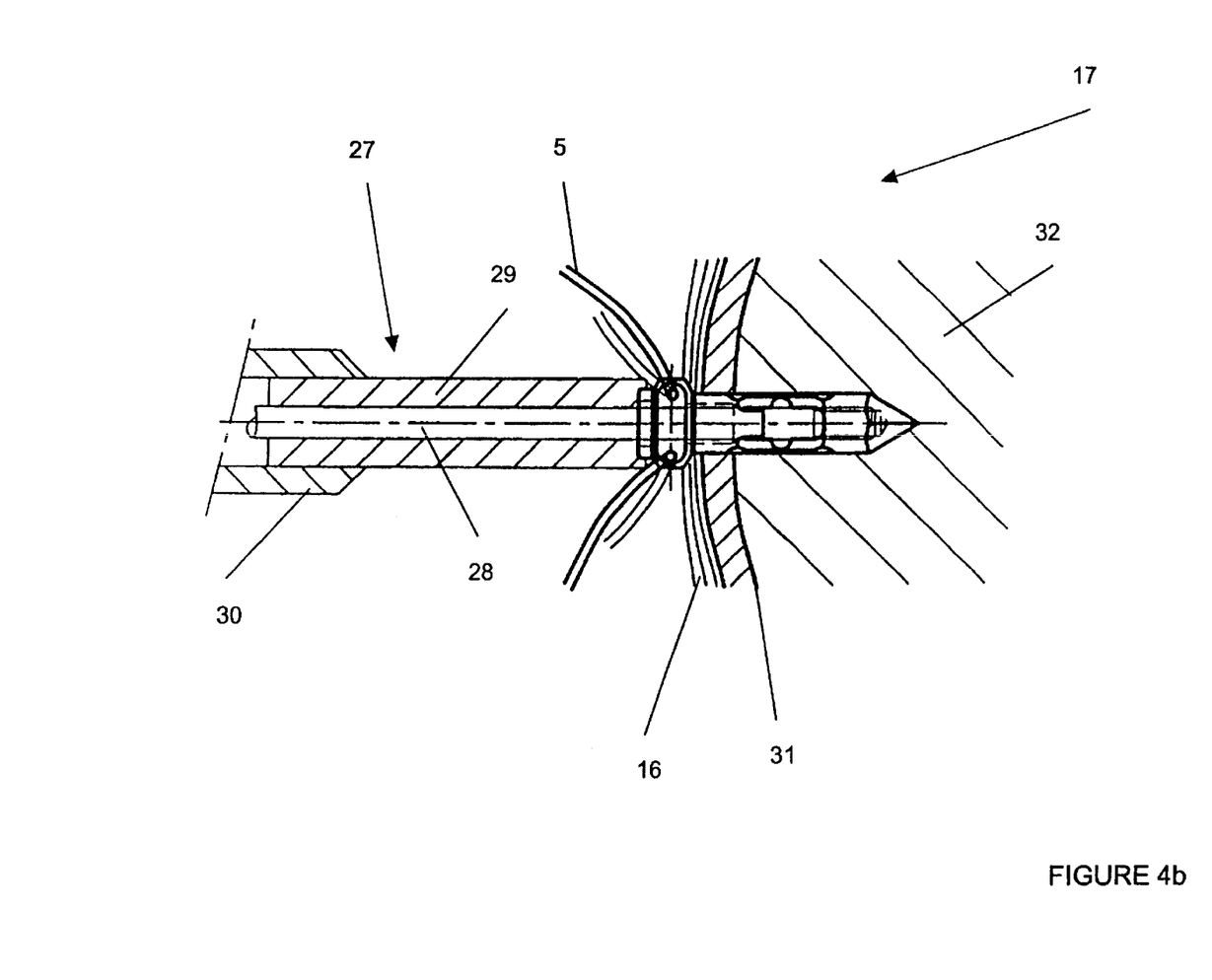

In FIG. 4b is illustrated the suture anchor 1 inserted into the surgical location by means of its attachment 27 and an arthroscopic cannula 30. The surgeon effectuates the setting of the suture threads 5 in the oblong clearance 20 of the means of fixation 4 be it prior to the insertion of the suture anchor 1 into the surgical location or after its placing into the bone 17.

The placing of the suture anchor 1 into the bone 17 is effectuated either by force, by rotation or by means of a preliminary hole drilled into the cortical bone 31 and the spongy bone 32 through the soft tissue 16 to be reinserted.

Figure 4C:
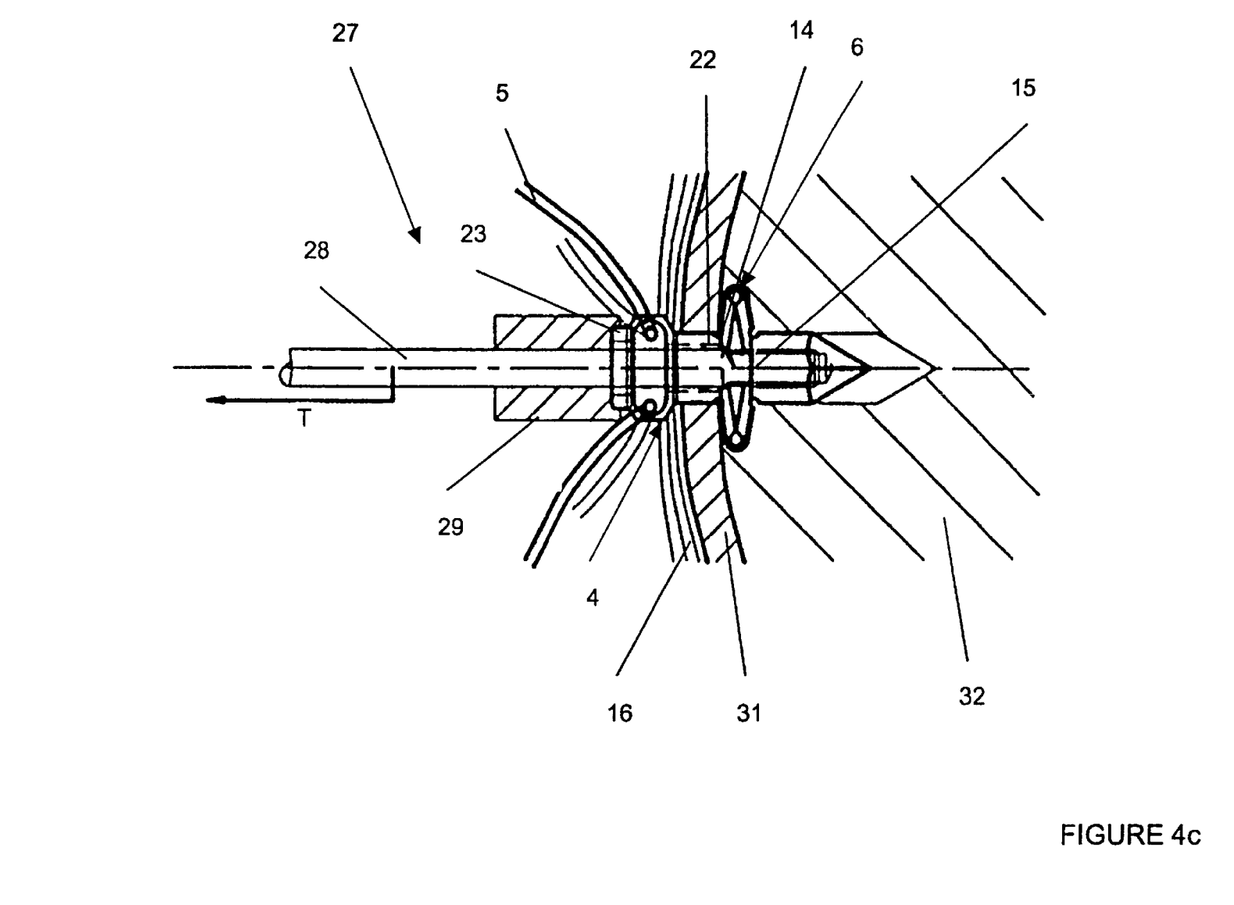

In FIG. 4c is illustrated the deformation of the suture anchor 1 and, in particular, of the prongs 6 and 7 inside of the spongy bone 32 when a tractive force T is applied to the rod 28 of the attachment 27. Thus, the rod 28 is horizontally displaced following the axis XX' of the body 2, while the sleeve 29 rests firmly against the surface 23 of the head 3.

The deformation of the prongs 6 and 7 is not limited until, because of its wall 15, the conical point 8 comes to rest against the stops 14.

The prongs 6 and 7 deform by virtue of a compression stress of the force T applied to the rod 28 of the attachment 27, following the shape of the fasteners 11, 12 and 13 so that the segments 6a, 6b and 7a 7b are directed towards the outside of the body 2 and in a direction approximately parallel to the axis XX'.

It can be noted that the fixation of the suture anchor 1 in the spongy bones is effectuated by the deformation of the prongs 6 and 7 until the segments 6a and 7a come into contact with the internal surface of the cortical bone 31.

Figure 4D:
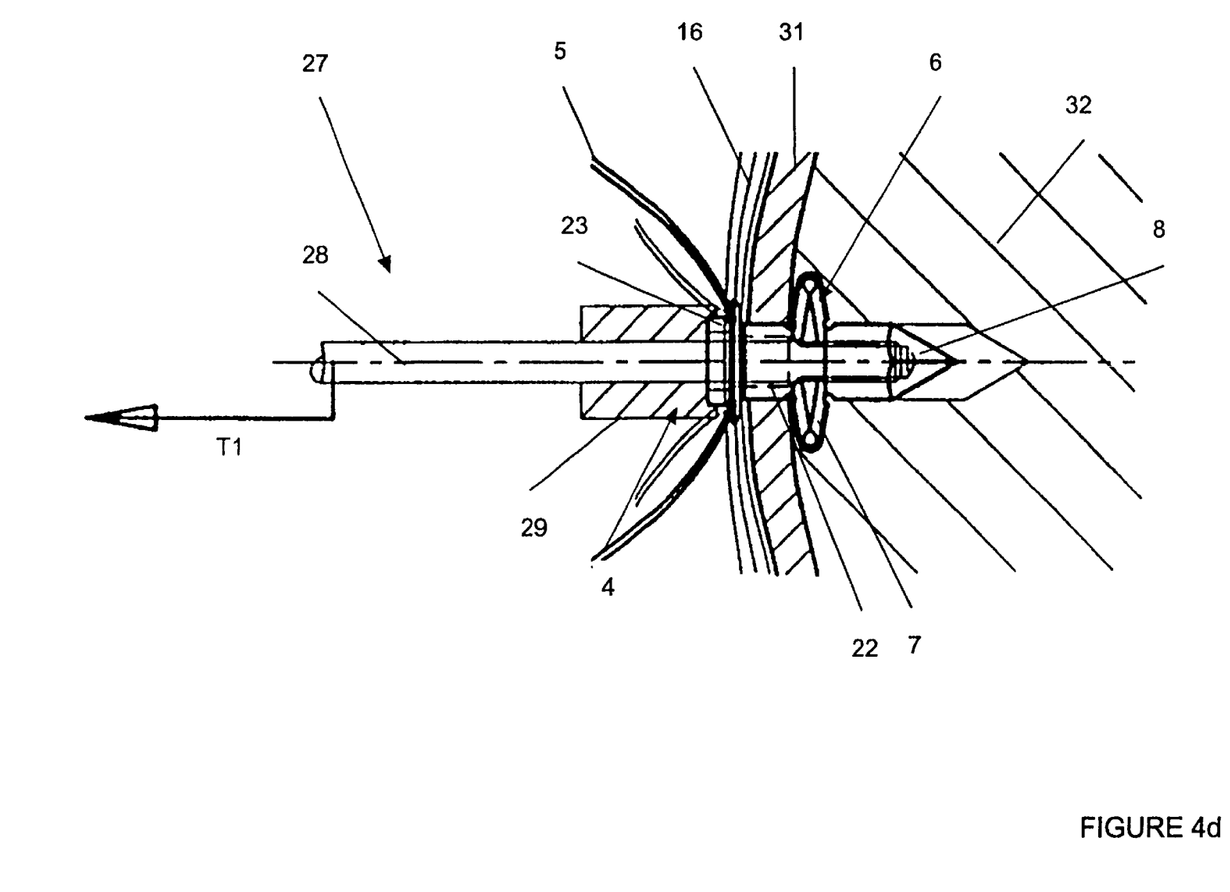

In FIG. 4d is illustrated the fastening of the suture threads 5 on the head 3 of the anchor 1 by the means of fixation 4.

Being the conical point 8 is in contact with the stops 14, it is possible to apply a tractile force T1 greater than that of T on the rod 28 of the attachment 27, without risking to break the prongs 6 and 7, in order to deform the tongues 18 and 19 of the means of fixation 4.

The deformation of the tongues 18 and 19 reduces the oblong clearance 20 in order to tightly fasten the suture threads 5 on the head 3 of the suture anchor 1.

The tongues 18 and 19 are designed so as not to cut the suture threads 5 when fastening them to the head 3.

The suture threads 5 enable the surgeons to ligature the soft tissues 16 to the suture anchor 1.

In FIGS. 5a to 5d are illustrated the various stages for the placing of the suture anchor 1 described above in FIG. 3 inside of the bone 17 for the fixation of the soft tissues 16.

Figure 5A:
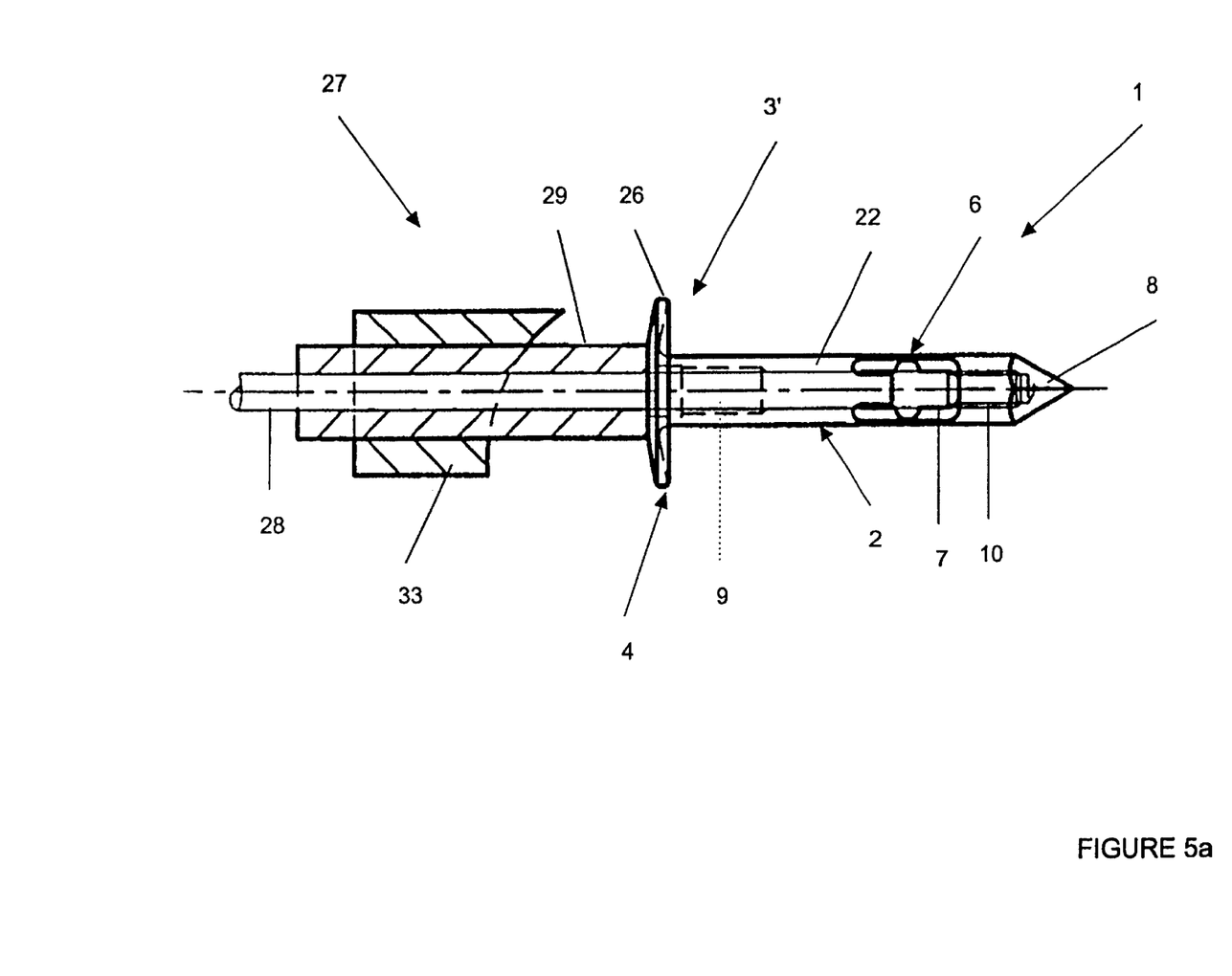
FIGS. 5a to 5d are diagrammatic views illustrating the placing of the embodiment of the suture anchor of FIG. 3.

In FIG. 5a is illustrated the suture anchor 1 with its attachment 27 for the setting into place, that is constituted, by way of example, by a rod 28 that traverses the body 2 to screw into the blind hole 10 of the conical shaped point 8. The rod 28 is affixed to a sleeve 29 that rests against the surface 23 of the head 3.

Around the sleeve 29 is provided a shaping device 33 of the disk 26 on the soft tissue 16.

Figure 5B:
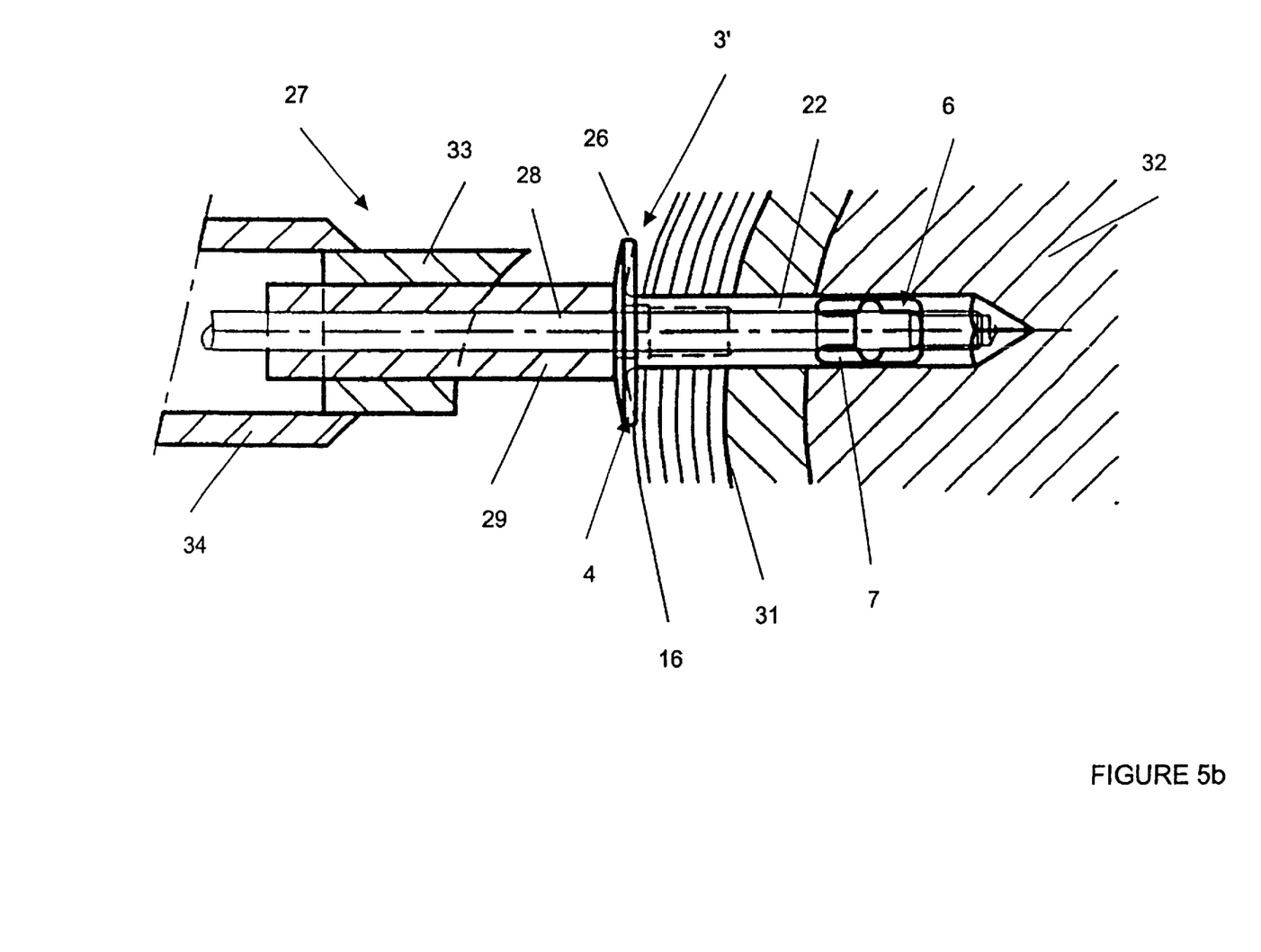

In FIG. 5b is illustrated the suture anchor 1 that is inserted into the surgical location by means of the attachment 27 and an arthroscopic cannula 34.

The placing of the suture anchor 1 into the bone 17 is effectuated either by force, by rotation or be means of a preliminary hole drilled into the cortical bone 31 and the spongy bone 32 through the soft tissue 16 to be reinserted.

Figure 5C:
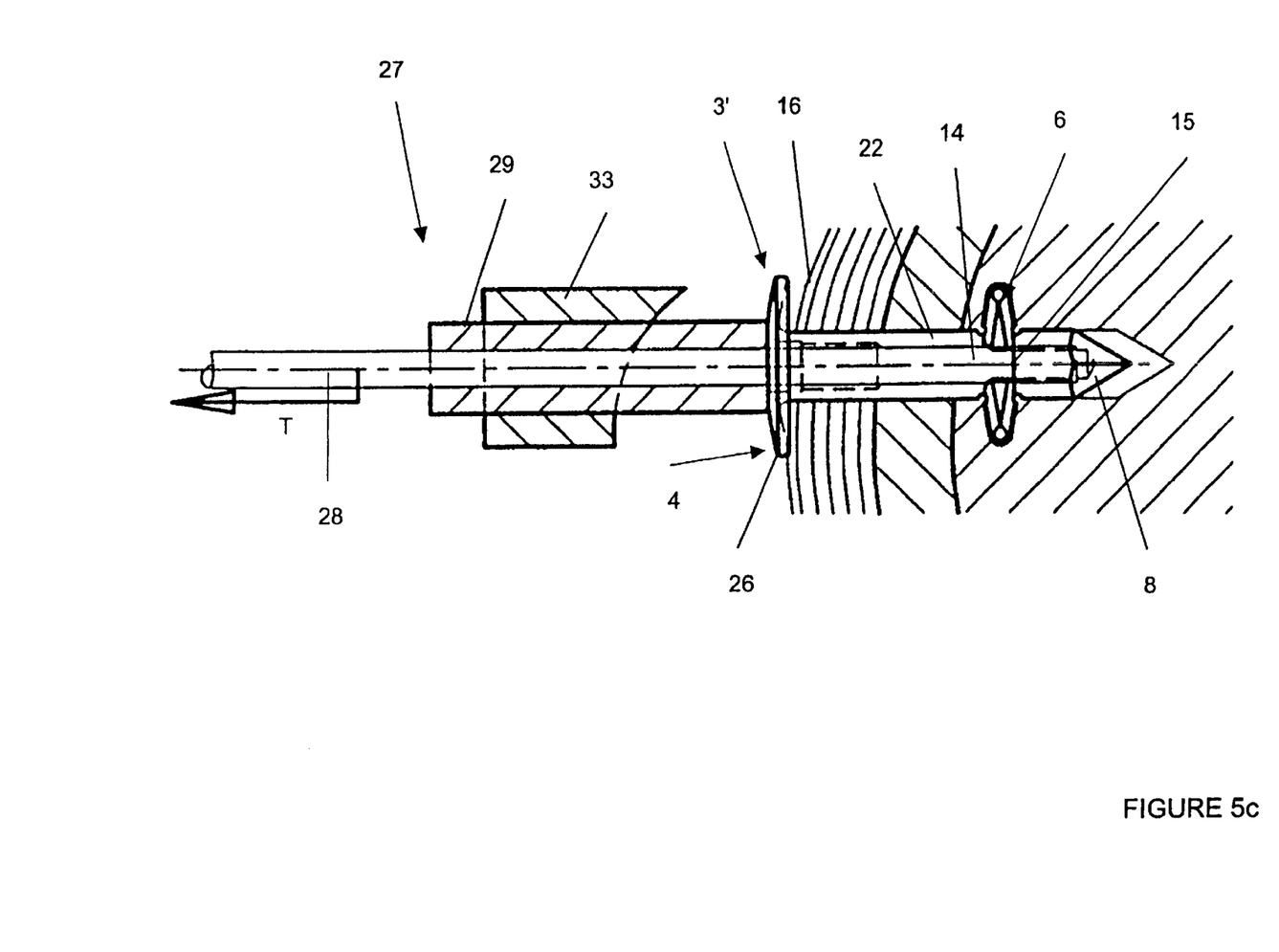

In FIG. 5c is illustrated the deformation of the suture anchor 1 and, in particular, of the prongs 6 and 7 inside of the spongy bone 32 when the rod 28 of the attachment 27 is subjected to a tractile force T. Thus, the rod 2 is horizontally displaced according to the axis XX' of the body 2, while the sleeve 29 continues resting against the disk 26 of the head 3'.

The deformation of the prongs 6 and 7 is delimited until the conical point 8, through its surface 15, comes to rest against the stops 14.

The prongs 6 and 7 deform by virtue of a compression stress of the force T applied to the rod 28 of the attachment 27, following the shape of the fasteners 11, 12 and 13 so that the segments 6a, 6b and 7a, 7b are directed towards the outside of the body 2 and in a direction approximately parallel to the axis XX'.

It can be noted that the fixation of the suture anchor 1 to the spongy bone 32 is effectuated by the deformation of the prongs 6 and 7 until the segments 6a and 7a come into contact with the internal surface of the cortical bone 31.

Figure 5D:
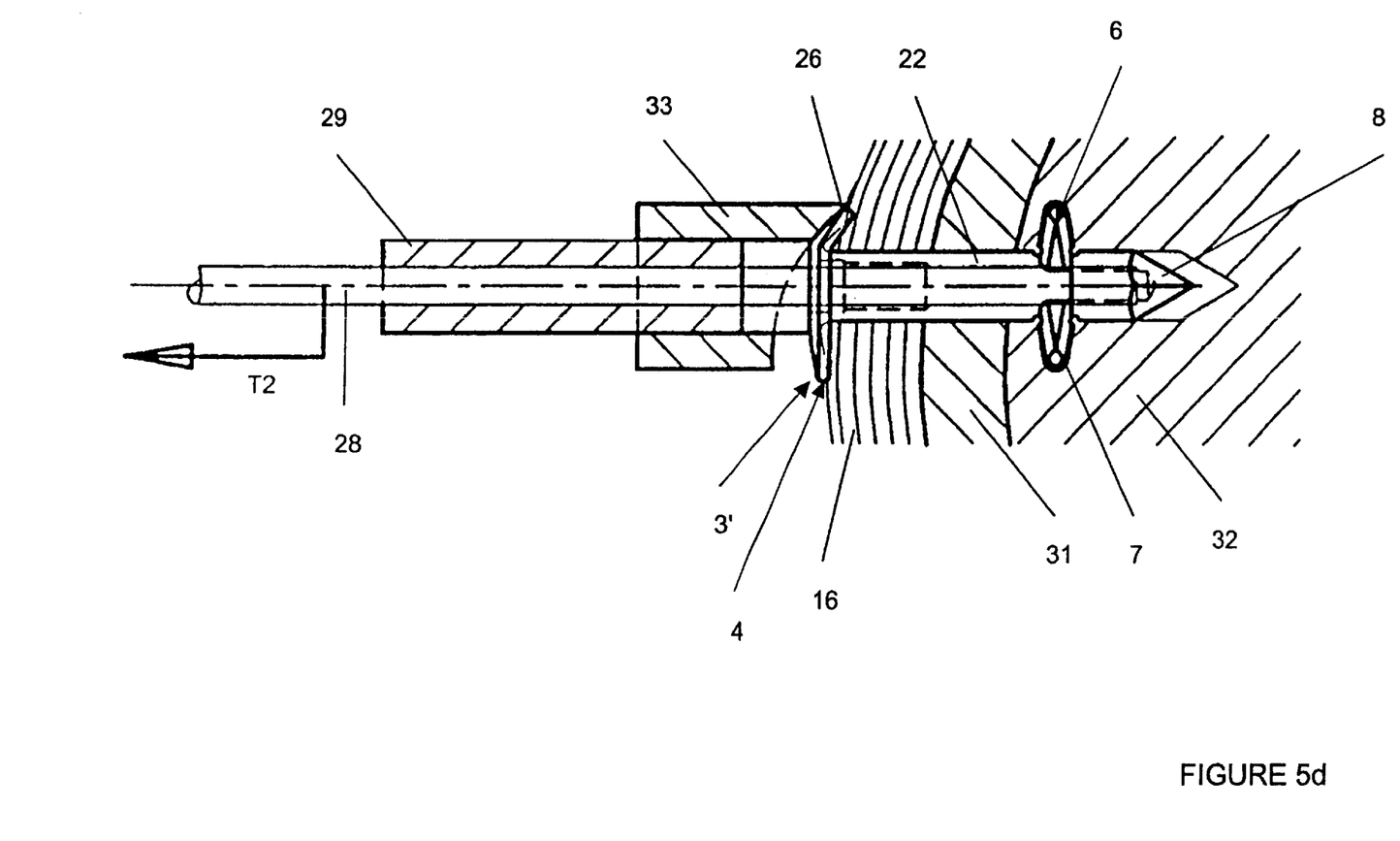

In FIG. 5d is illustrated the configuration of the disk 26 by the shaping device 33 after the previous withdrawing of the sleeve 29 in order to apply anew a tractive force T2 greater than that of T allowing the deformation of the prongs 6 and 7.

The force T2 enables the surgeon to bend the disk 26 of the head 3' so that it enters into the soft tissue 16 in order to adhere it to the cortical bone 31.

The configuration or bending of the disk 26 is effectuated in various stages. For the surgeon it suffices to unscrew the rod 28 in order to position the shaping device 33 in another direction, to screw anew the rod 28 into the hole 10 of the point 8 and to apply again the tractile force T2 in order to bend the disk 26.

In FIGS. 6a to 6d are illustrated the various stages for the removal of the suture anchor 1 from the bone 17 by means of another attachment 35. This attachment facilitates the removal of the suture anchor 1 provided with the head 3 or 3'.

Figure 6A:
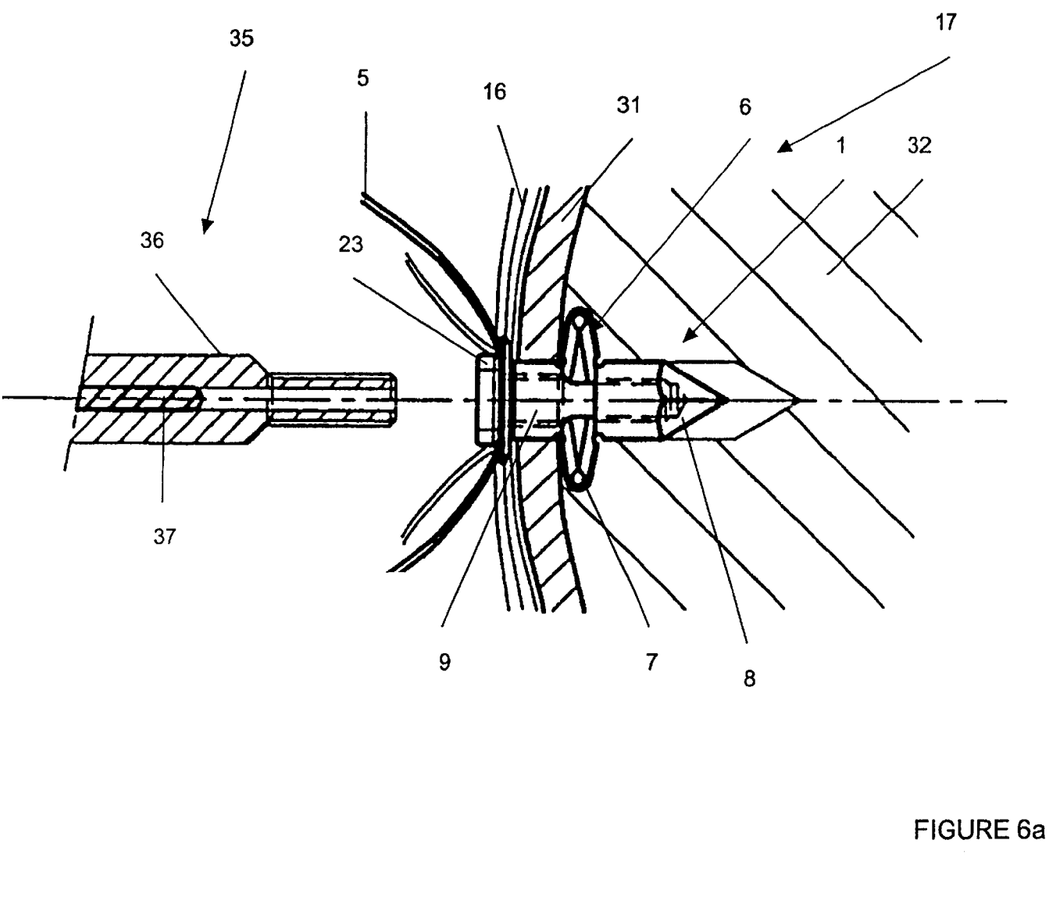
FIGS. 6a to 6d are diagrammatic views illustrating the removal of the suture anchor from the bone.
Figure 6B:
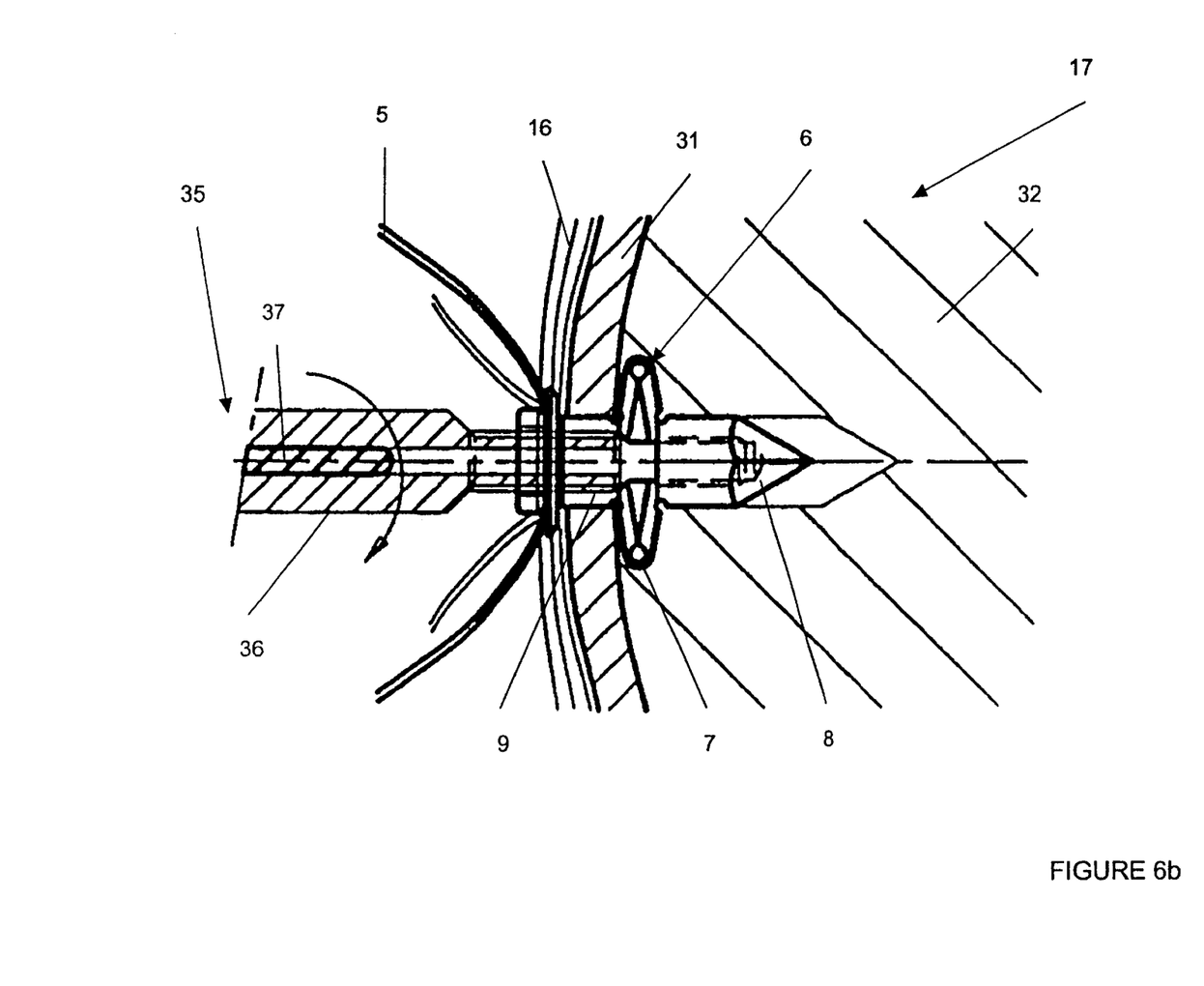

The attachment 35 comprises a hollow rod 36 that is screwed into the threaded borehole 9 of the cylindrical section 22, while another rod 37 sliding inside the first one comes to rest against the bottom of a blind hole 10 in the conical shaped point 8 (FIG. 6b).

Figure 6C:
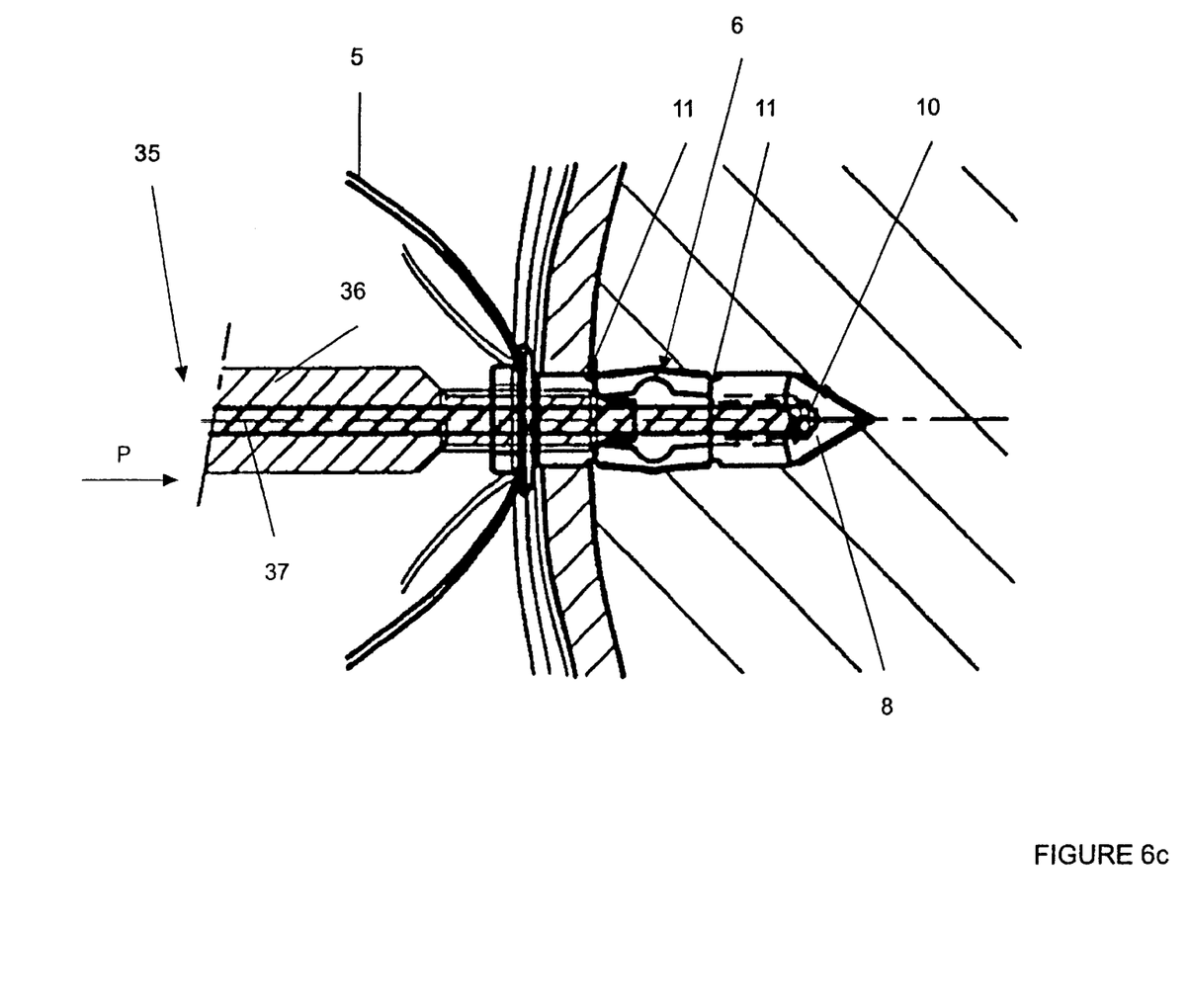

The rod 36 is subjected to a thrust force P parallel to the axis XX' of the body 2 in order to open the prongs 6 and 7 (FIG. 6c). The shape of the fasteners 11, 12 and 13 allows to return the suture anchor 1 to a shape similar to its original one.

Figure 6D:
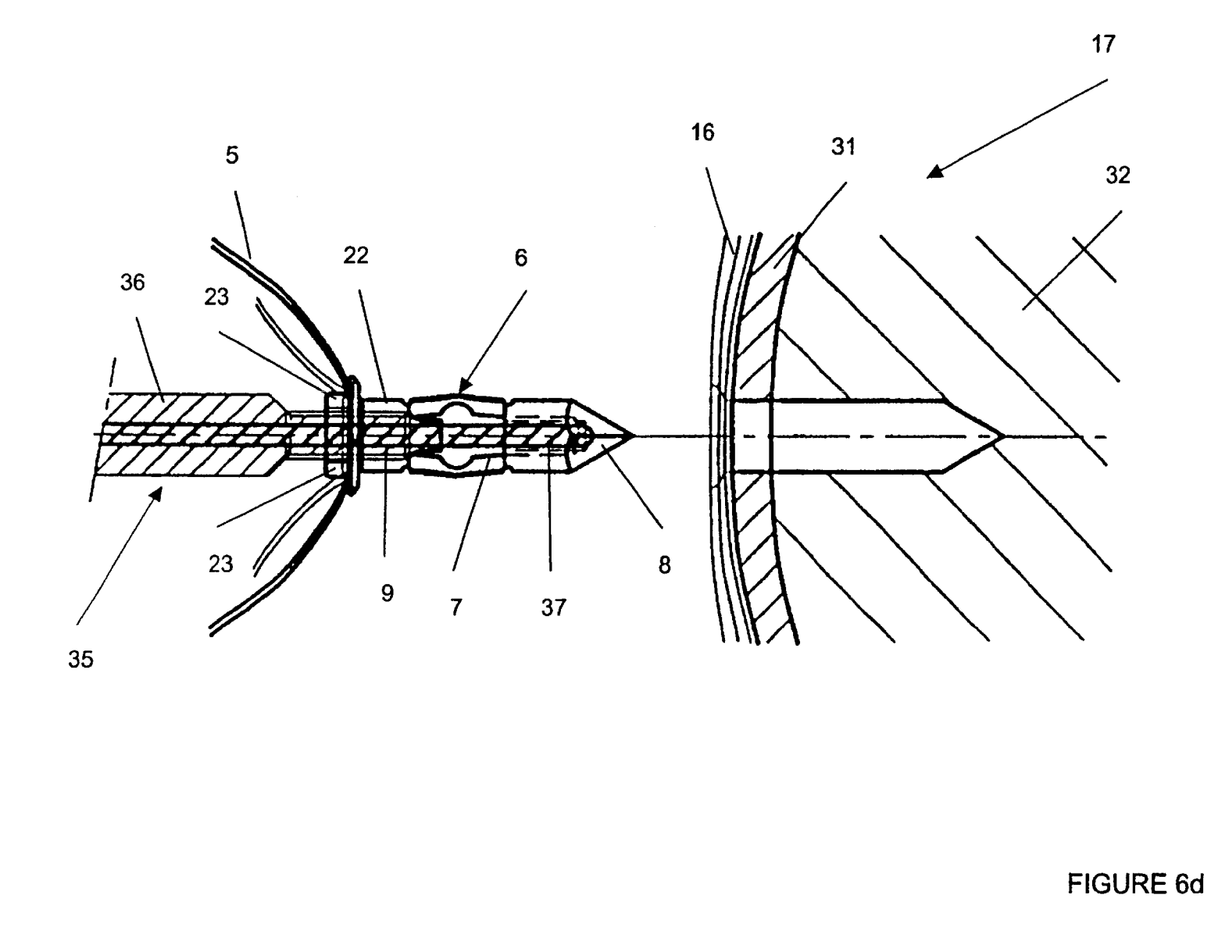

As soon as the suture anchor 1 has returned to an elongated position, the surgeon can remove the anchor from the bone 17 with the help of the attachment 35, without having to drill a hole the diameter if which is approximately that of the deformed prongs.

What is claimed is:

1. A suture anchor allowing the fixation of soft tissues against a bone which includes a monobloc hollow body (2) having expansion means (6, 7) which, under the effect of a first external tractive force (T) for the fixation of the suture anchor to the bone, are limited by stop means (14) in a plastic deformation, and the deformation of said expansion means (6, 7) being reversible by an external thrust force (P) applied thereto, which allows the removal of the suture anchor from the bone.

2. A suture anchor in accordance with claim 1, wherein said body includes means of fixation (4) for the binding of the soft tissues to the bone.

3. A suture anchor in accordance with claim 1 wherein the monobloc, hollow body (2) is provided at one its extremities with a head (3, 3') comprising means of fixation (4) for binding of the soft tissues to the bone, said expansion means being constituted by at least two fixation prongs provided on an extension of said head and parallel to a longitudinal axis (XX') of said hollow body prior to deformation, said stop means includes at least two stops inserted between each of said at least two fixation prongs for limiting the plastic deformation of the at least two prongs, and a conically shaped point (8) provided on said hollow body on an end thereo opposite said head.

4. A suture anchor in accordance with claim 3 wherein the means of fixation (4) is constituted by two tongues (18, 19) which are spaced on opposite sides of and generally parallel to the longitudinal axis (XX') of the hollow body (2) prior to deformation, said tongues define an oblong opening adapted to be traversed by at least one suture thread, whereby a suture thread may be is fastened to the head (3) after the deformation of the tongues (18, 19) by application of another tractive force, in order to facilitate the ligature of the soft tissues to the suture anchor.

5. A suture anchor in accordance with claim 3 wherein the head (3') is provided with means of fixation (4) constituted by a disk (26) arranged perpendicular to the longitudinal axis (XX') of the hollow body (2), and said disk being formed to bind the soft tissues against the bone.

6. A suture anchor in accordance with claim 3, wherein the hollow body (2) is provided at the conically shaped point (8) with a threaded blind hole (10) that receive a threaded rod (28) of an attachment (27) to deform, under the effect of the first tractive force (T), the at least two fixation prongs (6, 7) in a direction that is approximately perpendicular to the longitudinal axis (XX') of said body and, under a second tractive force (T1, T2) greater than the first tractive force (T), to deform the means of fixation (4).

7. A suture anchor in accordance with claim 3, wherein the in proximity of the head (3, 3') the hollow body is provided with an internal threaded borehole (9) that receives a first threaded hollow rod (36) of an attachment (35) and a second rod (37) slidable inside the first rod (36), said second rod being adapted to rest against a bottom of a threaded blind hole (10) so that, under a thrust force (P), the at least two fixation prongs (6, 7) are elongated thereby allowing withdrawal of the suture anchor from the bone.

8. A suture anchor in accordance with claim 3, wherein the at least two fixation prongs (6, 7) are connected to a cylindrical section (22) of the head (3, 3') and to the conical shaped point (8) by first bending fasteners (11) oriented toward the longitudinal axis of the body (2).

9. A suture anchor in accordance with claim 8, wherein the at least two fixation prongs (6, 7) are provided in a middle portion thereof with second bending fasteners (12, 13), respectively, that are inverted with respect to the first bending fasteners (11) so that each prong is constituted by two identical segments (6a, 6b; 7a, 7b).

10. A suture anchor in accordance with claim 7, wherein the internal threaded borehole (9) and the threaded blind hole (10) are oriented on the longitudinal axis (XX') of the body (2) and are of different diameters.

11. A suture anchor in accordance with claim 3, wherein the at least two stops extend parallel to the longitudinal axis (XX') of the body (2).

12. A suture anchor in accordance with claim 3, wherein the conical point (8) is provided with a surface (15) that is parallel to the axis (XX').

13. A suture anchor in accordance with claim 4, wherein the oblong opening (20) of the means of fixation (4) is positioned in such a manner that it has a longest side which is perpendicular to the longitudinal axis (XX') of the body (2).

14. A suture anchor in accordance with claim 4, wherein the head (3) is provided with a cylindrical section (22) which is provided at an external periphery thereof with a circular flange (24) shaped to form a support stop for the body (2) against an external wall of the bone.

15. A suture anchor in accordance with claim 5, wherein the head (3') is provided with a cylindrical section (22) including an internal borehole (9) having a threaded portion in proximity to the disk (26).

* * * * *